(12) United States Patent
Heusser et al.

(10) Patent No.: US 7,997,450 B2
(45) Date of Patent: Aug. 16, 2011

(54) MULTICOMPONENT CARTRIDGE

(75) Inventors: Rolf Heusser, Winterthur (CH); Andreas Staub, Winterthur (CH)

(73) Assignee: Sulzer Mixpac AG, Haag (CH)

( * ) Notice: Subject to any disclaimer, the term of this patent is extended or adjusted under 35 U.S.C. 154(b) by 808 days.

(21) Appl. No.: 11/900,308

(22) Filed: Sep. 10, 2007

(65) Prior Publication Data

US 2008/0083782 A1 Apr. 10, 2008

(30) Foreign Application Priority Data

Oct. 6, 2006 (DE) .......................... 10 2006 047 811

(51) Int. Cl.
*B67D 7/78* (2010.01)

(52) U.S. Cl. ...................... 222/145.6; 222/137; 222/459; 222/525; 239/402; 239/414; 433/90; 366/181.5; 366/339

(58) Field of Classification Search .................. 222/134, 222/136–137, 145.5–145.6, 519–525, 548–550, 222/459, 531–532; 239/304, 343, 402, 414, 239/416; 366/181.5, 189, 312, 336–340; 433/90

See application file for complete search history.

(56) References Cited

U.S. PATENT DOCUMENTS

| 4,538,920 | A | * | 9/1985 | Drake | 366/181.5 |
| 4,771,919 | A | * | 9/1988 | Ernst | 222/134 |
| 6,135,631 | A | * | 10/2000 | Keller | 366/339 |
| 6,834,782 | B2 | * | 12/2004 | Ritter | 222/521 |
| 2001/0015936 | A1 | * | 8/2001 | Heusser et al. | 366/337 |
| 2004/0104249 | A1 | * | 6/2004 | Horth et al. | 222/145.6 |

FOREIGN PATENT DOCUMENTS

| EP | 1 312 409 B1 | 5/2003 |
| EP | 1 430 959 A2 | 6/2004 |
| WO | WO 2006/005206 A1 | 1/2006 |
| WO | WO 2006/005213 A1 | 1/2006 |

* cited by examiner

*Primary Examiner* — Kevin P Shaver
*Assistant Examiner* — Andrew Bainbridge
(74) *Attorney, Agent, or Firm* — Francis C. Hand; Carella, Byrne, Cecchi

(57) ABSTRACT

The multicomponent cartridge has a container with chambers for the reception of different fluid components, a mixer element fixed on the container for the mixing of the components and a dispensing tube placed onto the mixer element and connected to the container for the dispensing of the mixed components. The mixer element is configured as a guide element for the axial displacement of the dispensing tube between an open position for dispensing of the mixed components and a closed position.

20 Claims, 5 Drawing Sheets

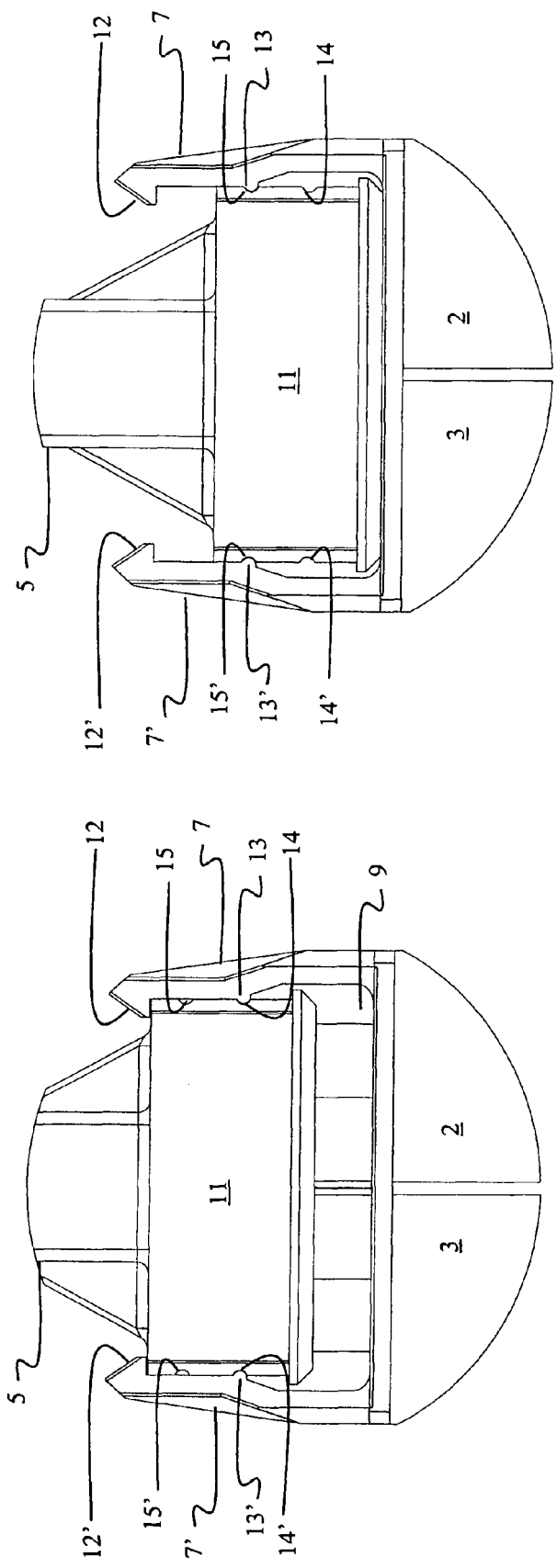

MULTICOMPONENT CARTRIDGE

This invention relates to a multicomponent cartridge. More particularly, this invention relates to a multicomponent cartridge for mixing separately stored multiple components.

DE 102 54 409 A1 describes a multicomponent cartridge for the mixing and dispensing of multicomponent products. The cartridge has a container with two chambers for two different flowable components, for example for dental purposes. To be able to mix the components prior to dispensing, a mixing coil is arranged at a cylindrical projection at one end of the chambers. This mixing coil is encompassed by a curved outlet tube arranged at a cap. The cap is rotatably placed onto a cylindrical projection of the chambers and can be rotated such that the curved outlet tube can be rotated in the direction desired for the dispensing of the components mixed in the outlet tube. For this purpose, the mixing coil is made flexible and curves, in each case, in the direction of the outlet tube. In the supply condition of the apparatus, the cap is in a closed state in which the cap closes the outlet openings of the chambers. To be able to dispense the components contained in the chambers, the components are pressed out by means of a piston, with the chamber moving from the closed position into an open position by the pressure of the components alone. This admittedly has the advantage that the dispensing tube can be brought into a suitable dispensing position by rotation, e.g. to apply dental material to or into the teeth of a patient. However, the installation of the cap is very difficult since the flexible mixing coil makes the fast and simple placing on of the cap with the dispensing tube difficult. For instance, the sensitive, flexible mixing structure would have to be carefully introduced into the dispensing tube while, simultaneously, necessarily watching the correct seat of the cap on the cylindrical projection. The displacement of the cap between the open and the closed position also contains the risk of the tilting of the cap and of damage to the mixing coil.

In order to simplify the placing of a dispensing tube onto a multicomponent cartridge, dispensing tubes provided with special coupling devices have been proposed in the prior art which can also be placed onto the chambers at a later time. DE 20 2006 004 738 U1 thus shows, for example, an apparatus for the mixing of two fluids in which two syringe parts can be reliably fastened to one another by means of an adapter element. A grommet with a mixing element arranged therein can be arranged at the side of the adapter element remote from the syringe parts, with them being connected by a coupling element similar to a bayonet fastening.

A further placeable dispensing structure with a mixer structure located therein is shown by EP 0 319 135 A2. Security against rotation is provided there by a dividing wall which is arranged at the syringe part and which engages in a corresponding slot at the dispensing tube. To prevent damage to the mixer element, the mixer element is arranged in the dispensing tube before the dispensing tube is mounted in place.

In none of the known apparatuses, however, is it ensured in a simple manner that the dispensing tube can be arranged cleanly on the syringe part without damaging the mixer element when being mounted in place. There is also the risk that the dispensing tube is not placed cleanly on the syringe part so that when the syringes are pressed out, the components can escape at the side at the connection points between the syringe parts and the dispensing tube.

Accordingly, it is an object of the present invention to provide a multicomponent cartridge which allows a simple and secure placing of a dispensing tube onto a container of the multicomponent cartridge as well as a moving to and fro between an open position and a closed position of the multicomponent cartridge.

Briefly, the invention is directed to a multicomponent cartridge that is comprised of a container having a plurality of chambers for the reception of different fluid components; a mixer element fixedly arranged on the container in communication with the chambers for receiving and mixing of the components from the chambers; and a dispensing tube mounted on the container about the mixer element for directing and dispensing the mixture of the components therefrom. In accordance with the invention, the dispensing tube is guided on the mixer element for axial displacement of the dispensing tube relative to the mixer element.

The placing on and displacement of the dispensing tube relative to the container can be advantageously enabled by having the mixer element configured as a guide element for the axial displacement of the dispensing tube.

To improve the displaceable guidance of the dispensing tube, the outer contour of the mixer element and the inner contour of the dispensing tube are matched to one another in an advantageous manner. Furthermore, in a particularly advantageous embodiment, the outer contour of the mixer element and the inner contour of the dispensing tube are matched to one another such that the dispensing tube can only be placed onto the mixer element in a predetermined position. In production, the dispensing tube can then no longer be placed on incorrectly, whereby a faulty placing of the dispensing tube on the mixer element is precluded. This can be achieved particularly easily in that the outer contour of the mixer element and the inner contour of the dispensing tube are rectangular or elliptical.

In this connection, a reliable guidance of the dispensing tube can additionally be made possible if the container has, at its end at the mixer side, a dispensing region of rectangular or elliptical shape which is engaged around by a correspondingly shaped step region of the dispensing tube.

To ensure a fixing of the dispensing tube in an open position and/or in a closed position of the dispensing tube holding elements, in particular latch noses and corresponding latch grooves, are provided on the container and/or on the dispensing tube. The components can hereby be dispensed without problem, on the one hand, and the chambers can be closed in a sealing manner, on the other hand, whereby a drying out or premature hardening of the components present in the chambers can be avoided. Dispensing openings of the chambers can particularly advantageously be sealingly closed by corresponding sealing elements arranged on the dispensing tube. In addition, the latch noses and latch grooves help the user to ensure that the dispensing tube is located in the correct position.

To avoid any accidental pulling of the dispensing tube off the container and to nevertheless permit a proper dispensing of the components from the chambers into the dispensing tube, securing elements are provided on the container and/or on the dispensing tube.

In an embodiment which is advantageous from a technical production aspect, the mixer element consists of a stable-shape material, so that the mixer element and the container are advantageously shaped in one single piece.

These and other objects and advantages of the invention will become more apparent from the following description taken in conjunction with the accompanying drawings wherein:

FIG. 7 illustrates a schematic view of the upper end of the container with a dispensing tube in the open position; and FIG. 8 illustrates a view similar to FIG. 7 with the discharge tube in the closed position.

Figure 1:
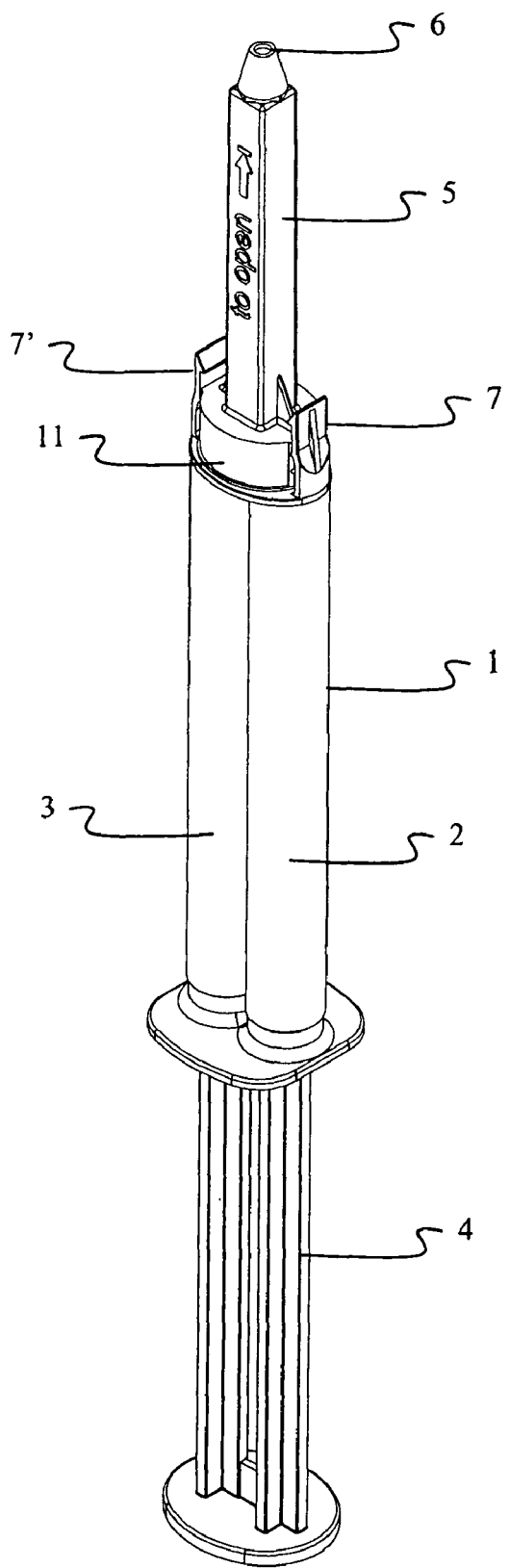
FIG. 1 illustrates a three-dimensional view of a multicomponent cartridge in accordance with the invention with a dispensing tube placed in a closed position.

Referring to FIG. 1, the multicomponent cartridge is configured as a dual syringe having a container 1 that has two substantially cylindrical chambers 2, 3 which are fixedly connected to one another for the reception of different components. The components may be the two components of a two-component adhesive which may only be mixed with one another before the application onto the articles to be glued. However, other components can also be stored in the chambers 2, 3, for example for dental applications.

The multicomponent cartridge has, as customary with dual syringes of this type, an expulsion plunger 4 which can be pressed from the end at the bottom in FIG. 1 towards the other end of the multicomponent cartridge in order to be able to press the components out of the chambers 2, 3.

A dispensing tube 5 is arranged at the other end of the chambers 2, 3 at the dispensing side. This dispensing tube 5 has a substantially square cross-section and a dispensing opening 6 for the dispensing of the mixed components.

The dispensing tube 5 is held in a closed position, as shown in FIG. 1, by correspondingly configured securing elements 7, 7', with the operation of the securing element 7, 7' being explained in detail later.

Figure 2:
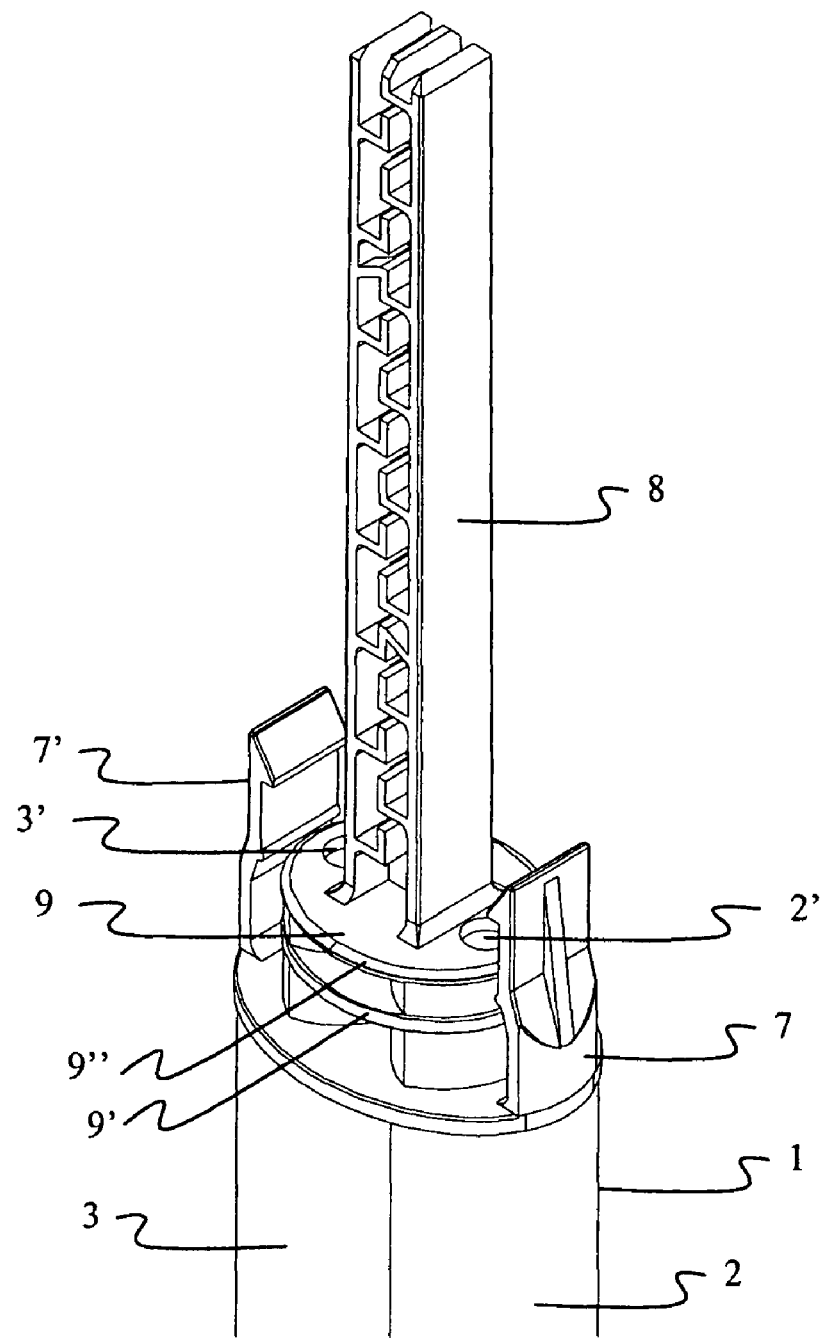
FIG. 2 illustrates a three-dimensional view of the multicomponent cartridge of FIG. 1 without a dispensing tube.
Figure 3:
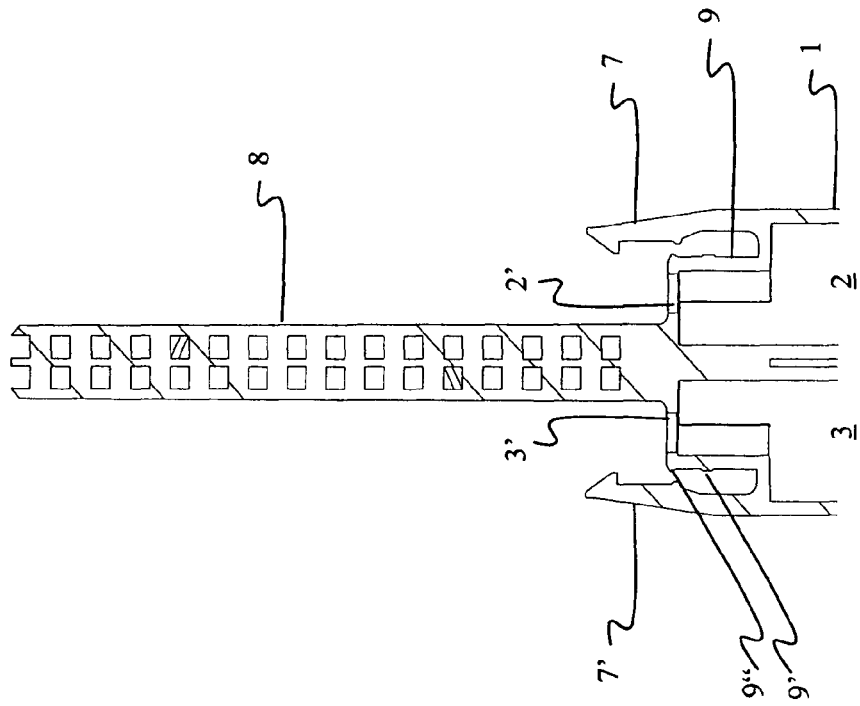
FIG. 3 illustrates a cross-sectional view through the end of a container of the multicomponent cartridge of FIG. 2 at the dispensing side without a dispensing tube.
Figure 6:
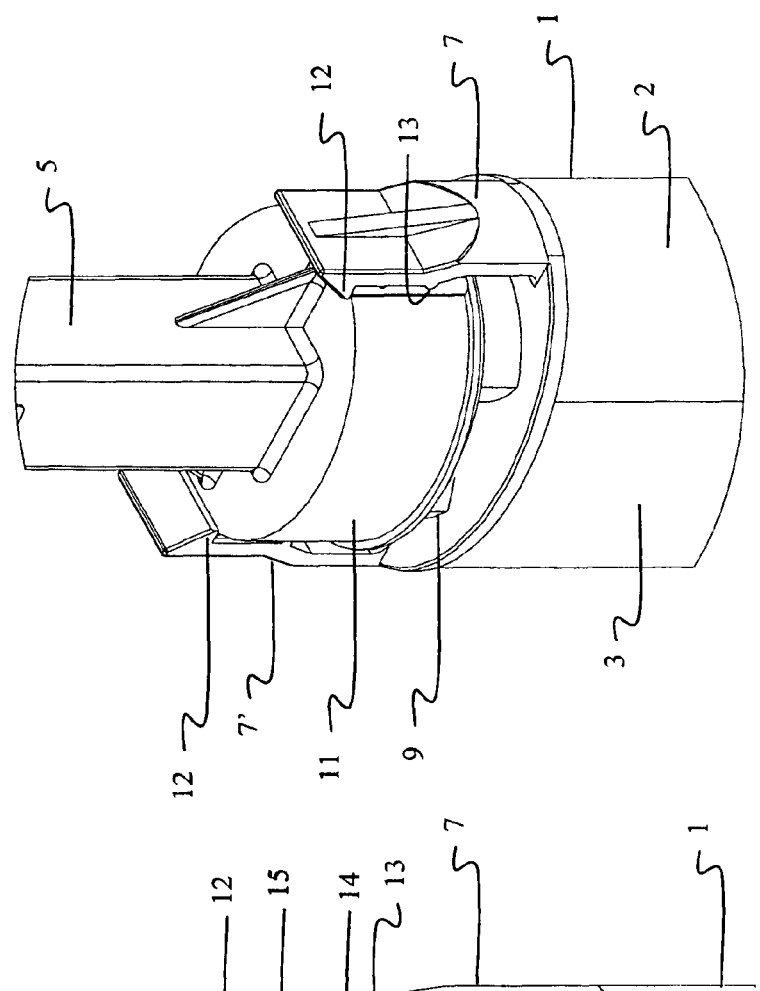
FIG. 6 illustrates a three-dimensional view corresponding to the detail of FIG. 5.

Referring to FIGS. 2 and 3, in which the end of the container 1 at the dispensing side is shown without the dispensing tube 5 in place, a mixer element 8 equipped with numerous deflection elements is provided at a substantially elliptically shaped dispensing region 9 of the container 1.

Figure 4:
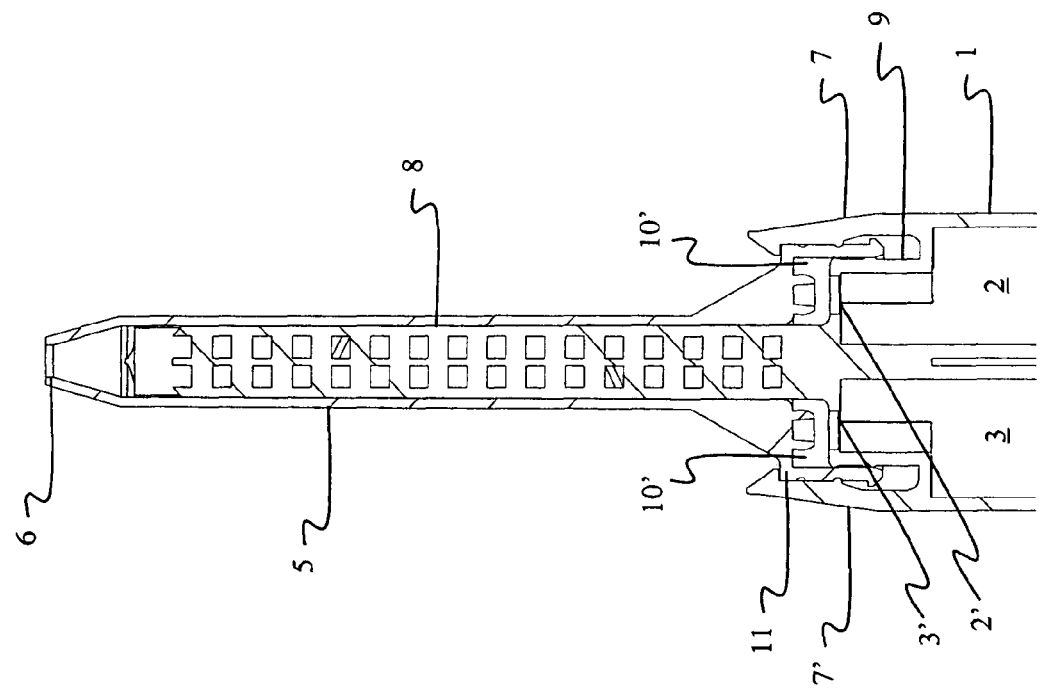
FIG. 4 illustrates a cross-sectional view similar to FIG. 3 with a dispensing tube in an open position.

Each chamber 2,3 of the container 1 has an outlet opening 2',3' at the top, as viewed, for dispensing a respective component therein into the dispensing region 9 of the container 1 and to the mixer element 8. In particular, as shown in FIG. 4, the outlet openings 2', 3' open into a mixing space 10, 10' formed by the dispensing tube 5 when mounted on the container 1 and when the dispensing tube 5 is in the open position.

Figure 5:
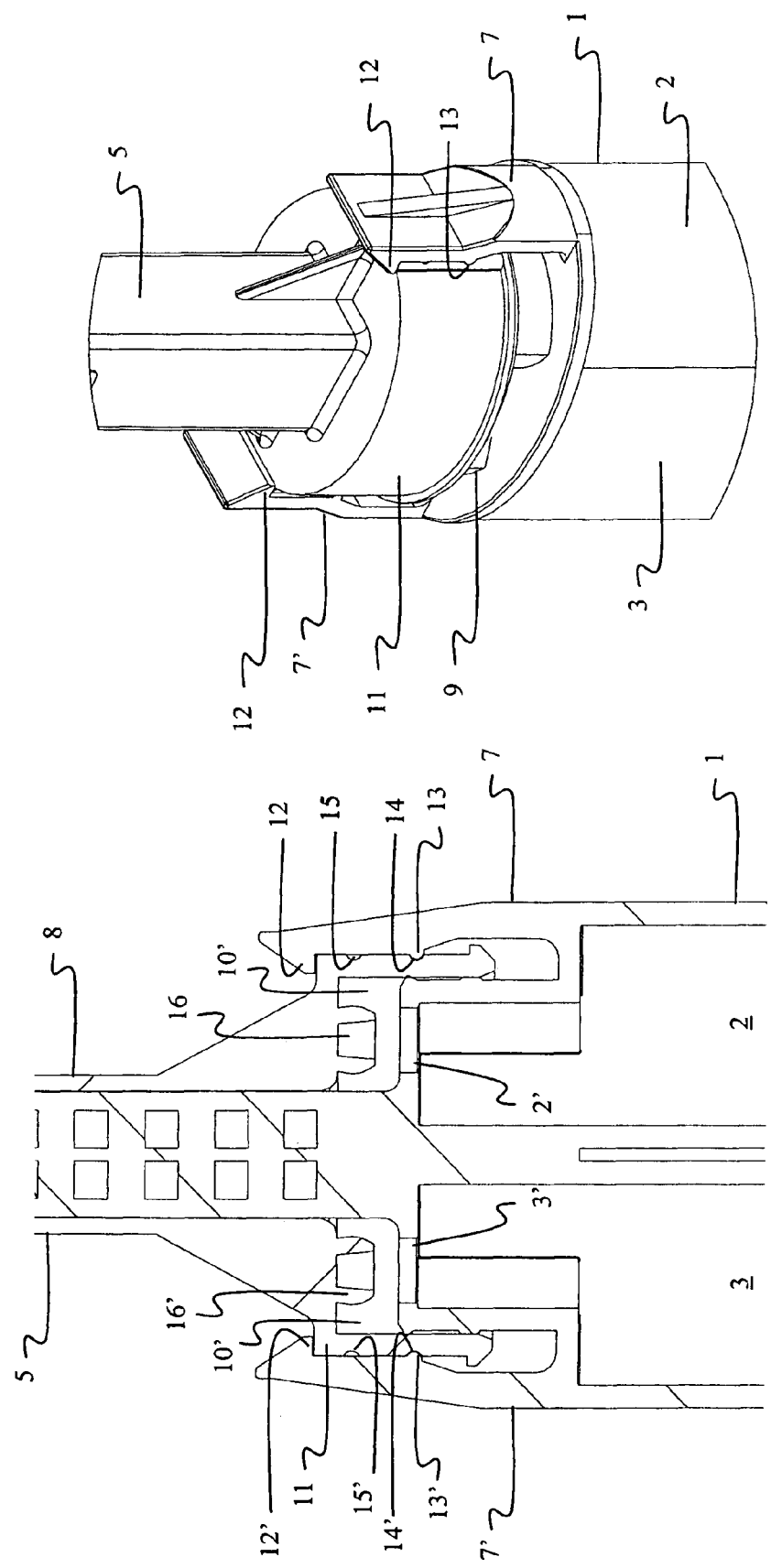
FIG. 5 illustrates a detailed cross-sectional view of the upper end of the container of FIG. 4.

As can be recognized particularly easily in FIG. 5, the components can flow into the substantially elliptical mixing space 10 by pressing in the expulsion plunger 4 towards the dispensing side of the container 1. Due to the pressure onto the components, they flow on through the mixer element 8 and the dispensing tube 5 towards the dispensing opening 6, while being mixed uniformly and efficiently in the mixer element 8.

The dispensing tube 5 has a shoulder region 11 at its end at the chamber side which is shaped correspondingly to the elliptically shaped dispensing region 9 of the container 1 and which, in particular, permits a secure guidance of the dispensing tube 5 from the open position into the closed position and back in cooperation with elliptical peripheral projections 9', 9''.

In order to prevent the dispensing tube 5 from being accidentally pulled off the container 1, e.g. when the dispensing tube 5 is opened, the securing elements 7, 7' have latch noses 12, 12' at their ends at the dispensing side. These latch noses are able to be pressed outwardly on the placing on of the dispensing tube 5 due to the flexibly configured securing elements 7, 7' and the chamfered ends of the shoulder region 11 at the chamber side. After the placing on of the dispensing tube 5, the latch noses 12, 12' then engage over substantially horizontal surfaces of the shoulder region 11 and thus prevent the dispensing tube 5 from being pulled off the container.

Referring to FIGS. 5 and 7, in order to hold the dispensing tube 5 in the open position, holding elements in the form of latch projections 13, 13' are provided on the securing elements 7, 7' and engage into corresponding latch grooves 14, and 14' in the dispensing tube 5.

Referring to FIG. 8, in order to also fix the dispensing tube 5 in the closed position, the shoulder region 11 of the dispensing tube 5 has additional latch grooves 15, 15' which in turn engage into the latch projections 13 arranged at the securing elements 7, 7'. These additional latch grooves 15, 15' are axially spaced from the latch grooves 14, 14'.

Referring to FIG. 5, in order to be able to sealingly close the dispensing openings 2', 3' in the closed position of the dispensing tube 5, the inner side of the shoulder region 11 has two substantially ring-shaped closing stoppers 16, 16' which converge inwardly towards the dispensing side and have the shape of a truncated cone in cross-section. Due to their special shape, the closing stoppers 16, 16' permit the closing of the dispensing openings 2', 3', with a specific force having to be overcome to pull the closing stoppers 16, 16' out of the dispensing openings 2', 3' in order to prevent, in addition to the holding elements 13, 13' and 14, 14', an accidental opening of the dispensing tube 5.

In the embodiment of the multicomponent cartridge shown in the drawings, the guidance of the dispensing tube 5 on the mixer element 8 is ensured by the square inner and outer contours which are matched to one another. The cross-section of both the mixer element 8 and of the dispensing tube 5 is therefore substantially square. For the components to be pressed through the mixer element 8 as completely as possible, the spacing between the inner contour of the dispensing tube 5 and the outer contour of the mixer element 8 is as small as possible, whereby a displacement of the dispensing tube 5 still has to be possible. In addition, an incorrect placing of the dispensing tube 5 on the mixer element 8 can be prevented by the alignment of the elliptical shape of the shoulder region 11, which can be easily recognized from the outside, and of the dispensing region 9 of the container 1. The mixer element 8 is made of a material of stable shape, i.e. a material that is rigid, such as a rigid plastic, a reliable guidance of the dispensing tube 5 only in the axial longitudinal direction of the multicomponent cartridge is ensured.

In an alternative embodiment of the invention, not shown in the drawings, the outer contour of the mixer element 8 and the inner contour of the dispensing tube 5 are rectangular, that is, each has a substantially rectangular cross-section so that a guidance of the dispensing tube 5 in a manner secure against rotation is already ensured hereby. In addition, it is advantageous with such an embodiment that the dispensing tube 5 can be placed on the mixer element 8 only in the position required for the secure sealing and engagement of the closing stoppers 16, 16' in the dispensing openings 2', 3'. In this case, the shoulder region 11 of the dispensing tube 5 and the dispensing region 9 of the container 1 can also have different shapes with different cross-sections, for example circular. It is nevertheless ensured by the specific shape of the mixer element 8 that the dispensing openings 2' or 3' and the stoppers 16, 16' engage into one another.

Instead of the securing elements 7, 7' with latch noses 12, 12' arranged thereon and shown in illustrated embodiment, other suitable securing means can also be provided. Instead of the latch grooves 14,14' or 15,15', corresponding latch projections 11 can be provided at the shoulder region of the dispensing tube 5, with then corresponding latch grooves having to be provided on the securing elements 7, 7' instead of the latch projections 13, 13'.

The invention thus provides a multicomponent cartridge which allows a simple and secure placing of a dispensing tube onto a container of the multicomponent cartridge as well as a moving to and fro between an open position and a closed position of the multicomponent cartridge.

What is claimed is:

1. A multicomponent cartridge comprising
a container having a plurality of chambers for the reception of different fluid components;
a mixer element fixedly arranged on said container in communication with said chambers for receiving and mixing of the components from said chambers therein; and
a dispensing tube mounted on said container in non-rotatable manner about said mixer element for directing and dispensing the mixture of the components therefrom, said dispensing tube being guided on said mixer element for axial displacement of said dispensing tube relative to said mixer element without rotation thereto.

2. A multicomponent cartridge in accordance with claim 1 characterised in that said dispensing tube has an inner contour matched to an outer contour of said mixer element for the displaceable guidance of said dispensing tube on said mixer element.

3. A multicomponent cartridge in accordance with claim 2 characterised in that said outer contour of said mixer element and said inner contour of said dispensing tube are matched to one another such that said dispensing tube can only be placed onto said mixer element in a predetermined position.

4. A multicomponent cartridge in accordance with claim 2 characterised in that said outer contour of said mixer element and said inner contour of said dispensing tube are each one of a complementary rectangular shape and a complementary elliptical shape.

5. A multicomponent cartridge in accordance with claim 1 further comprising a plurality of holding elements on one of said container and said dispensing tube for selectively holding said dispensing tube relative to said mixer element in one of an open position for dispensing of the mixed components from said dispensing tube and a closed position for sealingly closing said chambers.

6. A multicomponent cartridge in accordance with claim 5 wherein said holding elements include axially spaced apart latch grooves in one of said container and said dispensing tube and co-planar latch noses in the other of said container and said dispensing tube for selectively engaging in said latch grooves.

7. A multicomponent cartridge in accordance with claim 5 wherein each said chamber of said container has an outlet opening for dispensing a respective component therein to said mixer element and said dispensing tube has a plurality of stoppers, each said stopper being disposed to engage in and sealingly close a respective outlet opening in said closed position of said dispensing tube.

8. A multicomponent cartridge in accordance with claim 1 wherein said container has a dispensing region adjacent said mixer element of a shape selected from one of a rectangular shape and an elliptical shape and wherein said dispensing tube has a correspondingly shaped shoulder region engaged around said dispensing region.

9. A multicomponent cartridge in accordance with claim 1 further comprising a plurality of securing elements integral with one of said container and said dispensing tube for holding said dispensing tube on said container.

10. A multicomponent cartridge in accordance with claim 1 wherein said mixer element consists of a material of stable shape.

11. A multicomponent cartridge in accordance with claim 1 wherein said mixer element and said container are made in one single piece.

12. A multicomponent cartridge comprising
a container having a plurality of chambers for the reception of different fluid components;
a mixer element integral with and extending axially from said container, said mixer element being in communication with said chambers of said container for receiving and mixing of the components from said chambers therein; and
a dispensing tube mounted on said container in non-rotatable manner about said mixer element for directing and dispensing the mixture of the components therefrom, said dispensing tube being guided on said mixer element for axial displacement of said dispensing tube relative to said mixer element without rotation thereto between an open position for dispensing of the mixed components from said dispensing tube and a closed position for sealingly closing said chambers.

13. A multicomponent cartridge in accordance with claim 12 further comprising axially spaced apart latch grooves in one of said container and said dispensing tube and co-planar latch noses in the other of said container and said dispensing tube for selectively engaging in said latch grooves to hold said dispensing tube in one of said open position and said closed position.

14. A multicomponent cartridge in accordance with claim 12 wherein each said chamber of said container has an outlet opening for dispensing a respective component therein to said mixer element and said dispensing tube has a plurality of stoppers, each said stopper being disposed to engage in and sealingly close a respective outlet opening in said closed position of said dispensing tube.

15. A multicomponent cartridge comprising
a container having a plurality of chambers for the reception of different fluid components, each said chamber having an outlet opening for dispensing a respective fluid component therethrough;
a mixer element fixedly arranged on said container in communication with said outlet openings of said chambers for receiving and mixing of the components from said chambers therein; and
a dispensing tube mounted on said container in non-rotatable manner about said mixer element for directing and dispensing the mixture of the components therefrom, said dispensing tube being guided on said mixer element for axial displacement of said dispensing tube relative to said mixer element and said container without rotation relative to said mixer element between a closed position closing said outlet openings of said chambers to a flow of liquid component therefrom and an open position spaced from said openings to allow a flow of liquid component therefrom.

16. A multicomponent cartridge as set forth in claim 15 wherein said dispensing tube defines a mixing space with said container in said open position thereof and said openings open into said mixing space in said open position.

17. A multicomponent cartridge comprising
a container having a plurality of chambers for the reception of different fluid components and a dispensing region for receiving fluid components from said chambers;
a mixer element integral with and extending axially from said container, said mixer element being in communication with said chambers and extending from said dispensing region for receiving and mixing of the components from said chambers therein;
a dispensing tube mounted on said container in non-rotatable relation about said mixer element for directing and dispensing the mixture of the components therefrom, said dispensing tube having a rectangular cross-sectional shape complementary to said cross-sectional shape of said mixer element for guidance on said mixer element and axial displacement of said dispensing tube relative to said mixer element between a closed position on said container for sealingly closing said chambers and an open position for dispensing of the fluid components from said chambers; and
a plurality of securing elements on one of said container and said dispensing tube for holding said dispensing tube on said container.

18. A multicomponent cartridge in accordance with claim 17 wherein each said chamber of said container has an outlet opening for dispensing a respective component therein to said mixer element and said dispensing tube has a plurality of ring-shaped closing stoppers of conical cross-section, each said stopper being disposed to engage in and sealingly close a respective outlet opening in said closed position of said dispensing tube.

19. A multicomponent cartridge in accordance with claim 17 wherein each said securing element is flexible and has a latch nose at an end thereof engaging over said dispensing tube in said closed position thereof.

20. A multicomponent cartridge in accordance with claim 19 wherein said dispensing tube has a horizontal surface on a shoulder region thereof in engagement with said latch nose of each said securing element.

* * * * *

UNITED STATES PATENT AND TRADEMARK OFFICE
CERTIFICATE OF CORRECTION

Page 1 of 1

PATENT NO.         : 7,997,450 B2
APPLICATION NO.    : 11/900308
DATED              : August 16, 2011
INVENTOR(S)        : Heusser et al.

It is certified that error appears in the above-identified patent and that said Letters Patent is hereby corrected as shown below:

Column 5
Line 27, "with claim" should be -- with claim 1 --

Signed and Sealed this
Twenty-seventh Day of September, 2011

David J. Kappos
*Director of the United States Patent and Trademark Office*